United States Patent
Fuchs et al.

(10) Patent No.: US 9,719,128 B2
(45) Date of Patent: Aug. 1, 2017

(54) SELECTIVE ULTRASONIC LYSIS OF BLOOD AND OTHER BIOLOGICAL FLUIDS AND TISSUES

(71) Applicant: AdvanDx, Inc., Woburn, MA (US)

(72) Inventors: Martin Fuchs, Uxbridge, MA (US); Michelle Meltzer, Chelmsford, MA (US)

(73) Assignee: AdvanDx, Inc., Woburn, MA (US)

( * ) Notice: Subject to any disclaimer, the term of this patent is extended or adjusted under 35 U.S.C. 154(b) by 0 days.

(21) Appl. No.: 14/084,026

(22) Filed: Nov. 19, 2013

(65) Prior Publication Data
US 2014/0186832 A1    Jul. 3, 2014

Related U.S. Application Data

(63) Continuation of application No. PCT/US2012/038535, filed on May 18, 2012.

(60) Provisional application No. 61/488,434, filed on May 20, 2011.

(51) Int. Cl.
*C12Q 1/68*    (2006.01)
*C12Q 1/04*    (2006.01)
*C12N 13/00*   (2006.01)

(52) U.S. Cl.
CPC .......... *C12Q 1/6806* (2013.01); *C12N 13/00* (2013.01); *C12Q 1/04* (2013.01)

(58) Field of Classification Search
None
See application file for complete search history.

(56) References Cited

U.S. PATENT DOCUMENTS

| | | | |
|---|---|---|---|
| 2006/0275781 A1* | 12/2006 | Pham | C12N 7/00 435/6.16 |
| 2009/0275063 A1 | 11/2009 | Green et al. | |
| 2009/0325198 A1 | 12/2009 | Holets-McCormack | |
| 2010/0120085 A1* | 5/2010 | Hyman | C12Q 1/04 435/34 |
| 2010/0124763 A1 | 5/2010 | Walsh et al. | |
| 2010/0129814 A1 | 5/2010 | Walsh et al. | |
| 2010/0203521 A1 | 8/2010 | Klapperich et al. | |
| 2010/0255573 A1 | 10/2010 | Bond et al. | |

FOREIGN PATENT DOCUMENTS

| | | | | |
|---|---|---|---|---|
| EP | 0268575 A2 | | 5/1988 | |
| GB | WO 2009/063198 | * | 5/2009 | ............ B01D 43/00 |
| WO | WO-2009/015484 A1 | | 2/2009 | |
| WO | WO-2010/124001 A1 | | 10/2010 | |
| WO | WO-2013/023198 A2 | | 2/2013 | |

OTHER PUBLICATIONS

Granger et al., "Recovery of *Mycobacterium avium* subspecies *paratuberculosis* from the natural host for the extraction and analysis in vivo-derived RNA," *J. Microbiol. Meth.*, 57(2):214-249 (2004).
English abstract of EP 0268575-A2.

* cited by examiner

*Primary Examiner* — Karen Cochrane Carlson
*Assistant Examiner* — Jennifer M. H. Tichy
(74) *Attorney, Agent, or Firm* — McCarter & English, LLP; Jonathan M. Sparks; Jin Wang, Esq.

(57) ABSTRACT

The present invention features methods for selective lysis of endogenous cells in a biological sample. In preferred embodiments, the methods of the invention comprise contacting the biological sample with lysis solution, and subjecting the mixture to ultrasound, thereby selectively lysing the endogenous cells in the biological sample. The invention also features a lysis solution comprising Saponin and Proteinase.

30 Claims, 5 Drawing Sheets

Figure 1    Filterability of Whole Blood: Lysis Solution with and without Ultrasonic Treatment Figure 2    Coagulase Negative Staphylococcus Detected in Clinical Whole Blood Sample Figure 3    Platelet Detection Limits Figure 4  *Bacillus cereus* Detected in Platelet Concentrate Figure 5    *Staphylococcus aureus* (top) and *Serratia marcescens* (bottom) Dectected in Clinical Bronchoalveolar Lavage

SELECTIVE ULTRASONIC LYSIS OF BLOOD AND OTHER BIOLOGICAL FLUIDS AND TISSUES

REFERENCE TO RELATED APPLICATIONS

This application is a continuation application of International Patent Application No. PCT/US2012/038535, filed on May 18, 2012; which claims the benefit of the filing date, under 35 U.S.C. §119(e), of U.S. Provisional Application No. 61/488,434, filed on May 20, 2011, the entire contents of each of which are incorporated herein by reference.

FIELD OF THE INVENTION

This invention pertains to the field of detection, identification and characterization of microorganisms in complex, cell-containing biological fluids and tissues.

BACKGROUND

The ability to detect and characterize low levels of microorganisms in biological samples is valuable for many applications including diagnosing and treating infections in both humans and animals, infectious disease research, detecting food contamination and identifying the causative organisms, monitoring product quality during food processing, monitoring environmental quality and so on.

Culture is often used to facilitate the detection and characterization of microorganisms in biological samples. The samples are incubated in an atmosphere and at a temperature that is conducive to the growth of microorganisms, possibly with the addition of nutrient media to sample. Under these conditions, the microorganisms will multiply and can reach high concentrations. After growth to a sufficient concentration is achieved, a variety of methods can be used for the detection and characterization of the microorganisms. These methods include staining, fluorescence-in-situ-hybridization (FISH), polymerase-chain-reaction (PCR) and matrix-assisted-laser-desorption-ionization (MALDI) mass spectrometry. The drawback to culture is that it is slow, typically proceeding over many hours. Direct, i.e. non-culture, methods would therefore be preferred in those cases where rapid detection and characterization is important.

A range of bioanalytical methods rely on the lysis of cells for the release of intracellular components. Such components include organelles such as mitochondria, lysosomes, and endoplasmic reticulum, molecular assemblies such as microtubules and ribosomes and molecules such as proteins, carbohydrates and nucleic acids. Following lysis, the intracellular components can be subjected to analysis by for example electrophoresis, chromatography, mass spectrometry or optical spectroscopy. Likewise, molecular methods such as PCR, microarray analysis and sequencing rely on cell lysis for the release of intracellular DNA and RNA for amplification and other kinds of processing. To meet these needs, various cell lysis methods have been developed. Such methods include osmotic, chemical, mechanical (e.g. grinding with beads), hydrodynamic (e.g. pressure cell) and acoustic (i.e. sonication with ultrasound).

Ultrasound (acoustic waves beyond the audible range) has been used to lyse cells to release contents for molecular analysis often in conjunction with beads. See Seiter, J. A. and Jay, J. M. 1980[5]. U.S. Pat. No. 5,374,522 (Murphy et al.) describes the use of an ultrasonic bath to disrupt cells such as *Mycobacterium tuberculosis* in a sample to which beads of glass or other materials in the range of 50 microns to 1 mm have been added. Such disruption released RNA and DNA into solution for hybridization with genetic probes. In U.S. Pat. No. 6,431,476, Taylor et al. teach a method for disrupting cells or viruses in a chamber with an ultrasonic transducer. Chandler et al. (U.S. Pat. No. 6,506,584) teach treating liquid with ultrasound in a flow-through device. The treatment can include cell lysis. U.S. Pat. No. 6,686,195 (Colin et al.) teaches lysing cells in a tube brought into direct contact with a shaped sonotrode. In U.S. Pat. No. 6,881,541 Petersen et al. teach a method for extracting nucleic acid from a sample using ultrasound. In U.S. Pat. No. 6,887,693 McMillan et al. teach a method for lysing components of a fluid sample that have been captured on a solid support. In U.S. Pat. No. 6,893,879, Petersen et al. teach a method for extracting an analyte from a fluid sample. U.S. Pat. No. 6,939,696 (Llorin et al.) teaches disrupting microorganisms in a sonicator at high pH in a lube without beads. In these references, the goal is to disrupt or lyse cells, whether mammalian or bacterial, to release the cell content for analysis. Belgrader et al. (U.S. Pat. No. 7,541,166) describe an apparatus that allows a sample or parts of a sample to be moved into a sonication chamber multiple times, allowing differing sonication levels to be applied to more and less sensitive cells such as epithelial and sperm cells releasing their DNA for analysis at different times.

In analyzing cell-containing biological samples, it is sometimes advantageous to lyse a subpopulation of the cells present in the sample. For example, when it is desired to perform a differential analysis of the white blood cells in blood using a Coulter counter, it is convenient to lyse the red blood cells while leaving the white blood cells intact. Various lysis solutions have been developed to achieve this result. See for example, U.S. Pat. No. 3,874,852 (Hamill), U.S. Pat. No. 4,185,964 (Lancaster), U.S. Pat. No. 4,521,518 (Carter et al.), U.S. Pat. No. 5,284,940 (Lin et al.), and U.S. Pat. No. 5,958,781 (Wong et al.). It is worth noting that red blood cells lyse fairly readily compared to the white blood cells and selective red blood cell lysis can be accomplished simply with osmotic shock. Agents that selectively lyse bacteria but not mammalian cells have potential utility in combating infections. Oren and Shay studied melittin diastereomers that lyse bacteria but not mammalian cells'. Selective lysis can be useful for biological research. Grifantini and coworkers were able to isolate adherent bacteria co-cultured with epithelial cells for gene expression studies by selectively lysing the epithelial cells with saponin.[4]

Direct assays for the detection of microorganisms in biological fluids are often hampered by the presence of endogenous cells in high numbers. In general, such assays can be simplified if a method for selectively removing the endogenous cells were available. Zierdt and his colleagues published a lysis method in 1977[1]. This method uses a mild detergent solution containing an enzyme mixture (Rhozyme prepared from *Aspergillus oryzae* cultures). In a subsequent paper[2], Zierdt refined the solution by substituting the less toxic detergent Tween 20 for the Triton X-100 used in the original protocol. The Zierdt method is able to process a suitable volume of blood, 1 mL for example, in 1 hour, yielding a clear, red solution that can be filtered through a 0.6 micron track-etch filter 8 mm in diameter in approximately 3 minutes using a pressure differential of 2.5 psi. A key advantage of the Zierdt method is that the product is filterable through filters with pores small enough to retain microorganisms. Following filtration, the filter can be placed on a nutrient plate under suitable conditions, allowing colonies to grow from individual cells. The colonies can then be counted and further analyzed for the identity and antibiotic susceptibility of the organisms. Alternatively, FISH or other fluorescent labeling methods can be applied to the cells and fluorescence microscopy used to directly visualize the cells on the filter. This offers the possibility of rapid detection and identification of microorganisms in a range of complex samples including blood and other clinical specimens. Hence, a method that is able to selectively lyse mammalian cells faster than the Zierdt method would be advantageous.

In addition to the presence of cells, other constituents of biological samples can also hamper the detection of microorganisms. For example, bronchial samples are often highly viscous due to the presence of phlegm and other lung exudates. Urine specimens may contain significant amounts of protein as well as cells and mucus. These materials impede the detection of microorganisms by microscopic methods. Various reagents are used to overcome the obstacles to detection posed by these sample constituents. For example, N-acetyl-L-cysteine (NALC), combined with sodium citrate is a digestant that breaks up mucus in sputum and other bronchial samples. The sodium citrate stabilizes the NALC by binding heavy metal ions that may be present. Such reagents have proven to be useful, but their action is often slow and their effectiveness limited.

It is therefore an object of the present invention to provide a method for the rapid and efficient lysis of mammalian cells in biological samples while leaving microorganisms (bacteria and fungi) in the sample substantially intact.

It as a further object of the invention to provide a method for treating viscous, cell and protein containing biological samples to render them liquid and freely flowing without disrupting microorganisms that may be present.

It is a further object of the invention to provide a method for making highly cellular and/or viscous biological samples filterable through small pore size filters in order to retain and concentrate microorganisms on the filter for further analysis.

SUMMARY OF THE INVENTION

The present invention is directed to achieving the objectives above by means of the surprising discovery that endogenous mammalian cells in a biological sample can be rapidly and effectively lysed while leaving the cells of any microorganisms that may be present substantially intact by mixing the sample with a lysis solution as described herein and subjecting the mixed sample to high-frequency ultrasound of prescribed frequency, power, duty cycle and duration.

The invention is also directed to liquefying highly viscous biological samples in a rapid manner while preserving substantially all the microorganisms present in viable form, by mixing the sample with an appropriate lysis solution as described herein and subjecting the sample to high-frequency ultrasound of prescribed frequency, power, duty cycle and duration.

This invention also provides a method for rapidly and effectively capturing microorganisms in intact and viable form from highly cellular and/or viscous biological samples by mixing the sample with an appropriate lysis solution as described herein and subjecting the sample to high-frequency ultrasound of prescribed frequency, power, duty cycle and duration and filtering the treated sample through a filter.

DETAILED DESCRIPTION OF THE INVENTION

Described by the present invention are methods for selective lysis of endogenous cells in a biological sample and method for detecting, identifying, characterizing or quantifying microorganisms in a biological sample, where the sample comprises a mixture of endogenous cells and microorganisms. The present inventors have found that endogenous cells in a biological sample can be rapidly and effectively lysed while leaving the cells of any microorganism that may be present in the sample substantially intact.

The term "endogenous cells" is meant to refer to those cells that are produced by or originate from or are growing within an organism, tissue or biological sample. For example, in certain preferred embodiments, an endogenous cell may be a mammalian cell.

The term "biological sample" is meant to refer to cell containing samples. In certain embodiments, a biological sample may be a body fluid, for example, but not limited to, blood or blood fractions, blood culture fluid, respiratory secretions, cerebrospinal fluid, urine, stool, wound exudates and naso-pharyngeal fluid or mucus. In other embodiments, the biological sample may be platelets, platelet concentrate or a mammalian cell culture. In still other embodiments, the biological sample may be food or edible products.

In preferred embodiments, the phrase "substantially intact" is meant to mean that the microorganisms are viable (i.e. they are capable of growing) or that their cells appear to be intact when imaged under a microscope in either stained or unstained form. In related preferred embodiments, the phrase "substantially intact" is meant to refer to at least 40%, 45%, 50%, 55%, 60%, 65%, 70%, 75%, 80%, 85%, 90%, 95%, or more of the microorganisms in the sample are recovered.

In certain exemplary embodiments, the method comprises mixing the biological sample with a lysis solution, and subjecting the mixture to ultrasound at a controlled temperature, thereby selectively lysing the endogenous cells in the biological sample.

Selective Lysis

As mentioned above, a method for selectively lysing mammalian cells while leaving microorganisms intact was developed by Zierdt and his colleagues. The method, published in 1977, uses a mild detergent solution containing an enzyme mixture (Rhozyme prepared from *Aspergillus oryzae* cultures). 30 mL of blood mixed with conventional blood culture medium (brain heart infusion broth, sodium polyanethol sulfate, p-aminobenzoic acid, 3% $CO_2$) is mixed with 20 mL lysis solution (0.1% Triton X-100 in 0.01M $NaHCO_3$—$Na_2CO_3$ buffer with 3% of stock Rhozyme 41 solution) and incubated for 30 minutes at 37° C. Samples lysed in this manner are capable of being filtered through 0.45 micron pore size filters. Zierdt subsequently refined the solution by substituting the less toxic detergent Tween 20 for the Triton X-100 used in the original protocol. Later, Zierdt studied a variety of detergents useful in blood lysis for their efficacy in lysing blood and their toxicity to bacteria as components of blood culture media.[6] In addition to Triton X-100 and Tween 20, Brij 96 and digitonin performed well.

However, the Zierdt method has the drawbacks of a lengthy incubation, a large (10:1) dilution of the sample, and the presence of residual blood cell nuclei in the lysed sample.

Lysis Solutions

Lysis solutions can be useful in assays for microorganisms for the purpose of lysing endogenous cells as well as liquefying and clarifying mucus and phlegm containing samples. In addition to the Rhozyme-based lysis solution described above, various compositions of lysis solutions have been developed often containing detergents, enzymes, salts and buffering agents.

Saponins, produced by certain plants, are ambipathic glycoside detergent compounds that bind cholesterol. Saponins have been found to be particularly effective for the selective lysis of mammalian cells in microbial cell assays.

Gordon Dorn in U.S. Pat. No. 4,164,449 teaches a method of concentrating microbial cells from blood by lysing the blood with saponin, centrifuging the lysed blood and removing the residual blood components from the microorganisms that are now in the pellet. The saponin is preferably treated to remove toxic components according the method taught in U.S. Pat. No. 3,883,425 also by Dorn which uses ultrafiltration to remove low-molecular weight components considered to be toxic to microorganisms.

In U.S. Pat. No. 5,501,960, Dorn teaches the use of sodium polyanethol sulfonate in combination with purified saponin to improve the recovery of microorganisms from specimens containing blood components.

The Dorn method requires mixing the blood with the saponin-containing lysis solution followed by 30 minutes of centrifugation. After centrifugation, the majority of the supernatant is removed and discarded. The microorganism-containing pellet is resuspended and distributed onto growth media for culture. After culture, colonies can be counted and analyzed. While quantitative, this method requires overnight culture and is somewhat labor intensive.

In U.S. Pat. No. 5,043,267, Richards teaches the use of saponin to lyse blood containing phagocytosed pathogens to release degraded pathogen while leaving unphagocytosed pathogens intact. Antigens from the degraded pathogens are detected with an immunoassay while the intact pathogens are cultured for confirmation of the assay result. Richards extends the Dorn method and allows detection of certain microbial antigens in one hour. The antigens are cell membrane constituents (lipoteichoic acid and peptidoglycan) which are not very specific. The ability of this method to identify microorganisms is therefore limited.

According to the invention, lysis solutions can comprise detergents or detergents combined with proteinase. In particularly preferred embodiments, the lysis solution comprises a detergent and a proteinase. Detergents useful in the invention include, but are not limited to, saponin, nonionic surfactants such as Triton X-100 and polysorbate surfactants such as Tween 20. In preferred embodiments, detergent concentrations can range from 0.1 to 10%. Proteinases useful in the invention include proteinases derived from *Aspergillus* (e.g. *Aspergillus melleus*) which have broad enzyme activity and those with more specific activity like Streptokinase which speeds the dissolution of fibrin clots. Commercially available Proteinase from *Aspergillus melleus* in the range of 8 Units/mL to 160 Units/mL has been shown to work. Other enzymes can be combined with proteinase to promote the breakdown of certain biomolecules. Cholesterol esterase, lipase and DNase are examples of enzymes that can be used in combination with proteinase. Reducing agents such as TCEP can be helpful for liquefying mucoid samples by reducing the disulfide bonds in mucin strands. Chaotropic agents such as guanidinium chloride can also aid in the dissolution of mucin gels by disrupting non-covalent bonds. Hypotonic salt solutions can also promote lysis.

According to certain preferred exemplary embodiments, the present inventors have found that a combination of saponin with proteinase from *Aspergillus melleus* in a phosphate buffer is particularly effective.

Accordingly, the present invention features a lysis solution comprising a detergent and a proteinase, preferably a lysis solution comprising Saponin and Proteinase. In certain embodiments, the lysis solution further comprises a Sodium Phosphate buffer, pH 8.

The lysis solution preferably comprises 0.1%, 0.2%, 0.3%, 0.4%, 0.5%, 0.6%, 0.7%, 0.8%, 0.9%, 1.0%, 1.1%, 1.11%, 1.12%, 1.13%, 1.14%, 1.15%, 1.16%, 1.17%, 1.18%, 1.19%, 1.2%, 1.21%, 1.22%, 1.23%, 1.24%, 1.25%, 1.26%, 1.27%, 1.28%, 1.29%, 1.30%, 1.31,%, 1.32%, 1.33%, 1.34%, 1.35%, 1.36%, 1.37%, 1.38%, 1.39%, 1.40%, 1.41%, 1.42%, 1.43%, 1.44%, 1.45%, 1.46%, 1.47%, 1.48%, 1.49%, 1.50%, 1.55%, 1.60%, 1.65%, 1.70%, 1.72%, 1.75%, 1.80%, 1.82%, 1.85%, 1.90%, 1.92%, 1.95%, 2.0%, 2.2%, 2.5%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, or 10.0% Saponin. Preferably, the lysis solution comprises 1.15% Saponin.

The lysis solution preferably comprises 5.0, 5.25, 5.5, 6.0, 6.25, 6.5, 7.0, 7.25, 7.5, 8.0, 8.25, 8.5, 9.0, 9.25, 9.5, 10.0, 10.25, 10.5, 11.0, 11.25, 11.5, 12.0, 12.25, 12.5, 13.0, 13.25, 13.5, 14.0, 14.25, 14.5, 15.0, 15.25, 15.5, 16.0, 16.25, 16.5, 17.0, 17.25, 17.5, 18.0, 18.25, 18.5, 19.0, 19.25, 19.5, 20.0, 20.25, 20.5, 21.0, 21.25, 21.5, 22.0, 22.25, 22.5, 23.0, 23.25, 23.5, 24.0, 24.25, 24.5, 25.0, 25.25, 25.5, 26.0, 26.25, 26.5, 27.0, 27.25, 27.5, 28.0, 28.25, 28.5, 29.0, 29.25, 29.5, 30.0, 31.25, 31.5, 32.0, 32.25, 32.5, 33.0, 33.25, 33.5, 34.0, 34.25, 34.5, 35.0, 35.25, 35.5, 36.0, 36.25, 36.5, 37.0, 37.25 or 37.5 Units Proteinase. In preferred embodiments, the lysis solution comprises 11.25 Units Proteinase.

Buffer concentrations from 0.01M to 0.1M have been tested. Tris and RNase running buffer have been used in place of sodium phosphate buffer. Accordingly, in further related embodiments, other buffers known to one skilled in the art can be used. It is therefore likely that other buffers can be substituted.

In certain preferred embodiments, the lysis solution comprises
  0.1M Sodium Phosphate buffer, pH 8;
  1.15% Saponin; and
  11.25 Units/mL Proteinase.

In further preferred embodiments, the Saponin is from *Quillaja* bark. Preferably, the Proteinase is from *Aspergillus melleus*.

In other exemplary embodiments, the lysis solution comprises
- 0.1M Sodium Phosphate buffer, pH 8
- 1.15% Saponin from *Quillaja* bark (Sigma S4521-25G)
- 11.25 Units/mL Proteinase from *Aspergillus melleus*, Type XXIII (Sigma P4032-25G)

Sonics

As mentioned above, ultrasound has been used to lyse cells to release the intracellular contents for molecular analysis. Beads of glass or other materials are often added to the sample to increase the mechanical action of the ultrasound. Transducers of various shapes have been used. In the prior work the outcome has been the comprehensive lysis of all the cells in the sample. By contrast, in the methods of the present invention the selective lysis of particular cell populations is achieved.

Two rather different types of ultrasound generating equipment are available. They are distinguished by the operating frequency. One type operates in the frequency range of 20 kHz (just above the range of human hearing) to about 80 kHz. The other type operates in the frequency range of 500 kHz to 1.5 MHz or higher and is often called megasonics. In the former, the wavelength of the sound waves ranges from about 80 mm to about 20 mm; while in the latter, the wavelength ranges from about 3 mm to about 1 mm. The shorter wavelengths produced in the megasonic range allow better localization of the sonic energy to the biological sample that may have a volume of approximately 1 cm$^3$. Moreover, bubbles produced by cavitation will generally be smaller at higher frequencies since the shorter cycles give them less time to grow before they collapse in the compressive phase of the cycle. As used herein, the term "high frequency ultrasound" is meant to refer to ultrasound in the megasonic range.

Some embodiments described below employ the Covaris S2 high frequency ultrasound system. In that system, a concave transducer is used to focus the acoustic energy on the sample. The transducer operates in a water bath in which the sample tube is immersed. The acoustic energy is coupled to the sample by the water. The system operates at approximately 500 KHz in a pulsed mode. The number of cycles per burst, the duty cycle, time duration and the intensity are settable on the instrument.

Covaris Settings:

The following settings have been found to provide optimum results with the Covaris S2.

Heat water bath to 37° C.

Degas water bath for 30 min prior to use per manufacturer's instruction.

Mix 1 mL of blood with 1 mL of lysis solution in a 3 mL round-bottom glass tube. Treat sample for 100 seconds at 10% duty cycle, 1 intensity, 1000 cycles/burst. Treat sample for 60 seconds at 10% duty cycle, 2 intensity, 1000 cycles/burst. Treat sample for 60 seconds at 10% duty cycle, 2 intensity, 200 cycles/burst.

Lower intensity (intensity setting 1) can be used in the last two steps if the duration is increased.

Other embodiments use a non-focused, high-frequency ultrasound system manufactured by ProSys, Inc. In this system, a planar transducer emits a directed beam of ultrasound. The diameter of the beam is governed by the size of transducer. The system operates at approximately 1 MHz. The duty cycle, time duration and the intensity are settable on the instrument. Sonic energy from the transducer can be coupled into the biological sample by water, a gel, or an elastomer.

ProSys Settings:

The following settings have been found to provide optimum results with the ProSys.
- 100 ms Pulse
- 50% Duty Cycle
- 45 Watts
- 5 minute duration The present inventors have found that when used as described above, these systems are effective in achieving the selective lysis of mammalian cells while leaving microorganisms intact and viable.

Systems operating at lower frequencies (20 to 40 kHz) are available from other suppliers such as Branson Ultrasonics. These do not focus the acoustic energy with a focusing transducer but can concentrate the energy with a transducer probe having a narrow tip. Our experience with these systems has shown them to be much less effective in lysing blood cells than the high frequency systems.

Filtration

It can be advantageous to filter lysed samples through filters having pores sufficiently small to retain microorganisms in the sample. As previously mentioned, the retained microorganisms can be supplied with nutrients and grown into colonies on the membrane for counting and further analysis or they can be visualized on the filter by fluorescence microscopy following treatment with fluorescent probes or antibodies. 0.6 micron and 0.45 micron filters are commonly used to capture bacteria and fungi from liquid samples. 0.45 micron and 0.2 micron filters are commonly used for filter sterilization of water and media. Blood and other cell-containing biological samples are not directly filterable with these filters because the filters are rapidly clogged by these highly cellular liquids. Filterability is a good measure of the effectiveness of a lysis procedure.

Various types of filters can be used. Membrane filters made of nylon, polycarbonate, polyester and aluminum oxide have been used. Track-etch membranes of polycarbonate or polyester are useful if it is desired to image microorganisms in a sample after the lysis procedure. These membranes feature smooth, flat surfaces with well-controlled cylindrical pores. Anopore (aluminum oxide) filters are also flat with well-controlled pores and thus useful for imaging. Pore sizes from 0.2 to 1 micron are effective for retention of bacteria and yeast with 0.45 to 0.8 micron being most useful. Larger pore sizes (up to 4 microns) can be used if only yeast (fungi) are of interest.

Detection and Identification of Microorganisms

Various assays for the detection and identification of microorganisms have been developed. Three general classes of assays are in common use. The first class encompasses culture-based methods whereby any microorganisms present in the biological sample are allowed to grow perhaps with the admixture of nutrient media into the sample. The growth of the microorganism(s) can be detected in various ways, such as by changes in the turbidity or the pH of the sample or by the evolution of $CO_2$ driven by the metabolic activity of the microorganisms during their growth. Microorganisms can be identified on the basis of which of a range of biochemical nutrient sources they are able to utilize for growth. Likewise, their resistance to various antibiotics can be assessed by characterizing their ability to grow in the presence of different concentrations of the antibiotics of interest. Culture-based methods are widely used for both identification and characterization of microorganisms. The primary disadvantage of these methods is the length of time (8 to 24 hours) required to get results.

The second class of assays involve the use of stains, binding agents or probes to confer a detectable color or label to the cells of any microorganisms that may be present. Microscopic examination is generally used to visualize the colored or labeled cells.

The Gram stain is an example of a stain that is commonly used in microbiology. It involves the use of crystal violet and iodine to stain fixed bacterial cells. Gram positive bacteria can be distinguished from Gram negative bacteria by their ability to retain the purple color of the crystal violet stain after washing with alcohol or acetone. Gram negative bacteria lose the purple color during the wash and are stained pink by the counter-stain, usually safranin or basic fuchsin, applied after the wash.

Antibodies are examples of binding agents. Antibodies that recognize and bind to bacterial cell-surface molecules have been developed. Such antibodies can be chemically modified to incorporate fluorescent tags. They can be utilized in assays such as direct fluorescence assays (DFA) in which one or more fluorescently tagged antibodies are mixed with the biological sample to be tested and incubated to allow antibody binding. Following a wash step, the sample is examined with a fluorescent microscope to detect cells to which the fluorescent antibodies have bound. Other examples of binding agents include aptamers, peptides, lectins and phages.

Probes are molecules that incorporate nucleobases. They can bind to DNA or RNA by hydrogen bonding of the nucleobases in the probe to complementary nucleobases in the DNA or RNA in a process called base pairing. Probes can be made up of DNA, PNA (peptide nucleic acid), LNA (locked nucleic acid), and related molecules and combinations thereof. The number and sequence of the nucleobases in a probe determine what target sequence the probe will bind to according to the rules of base pairing, as well as the strength and specificity of the binding. The strength of the binding under various conditions of salt concentration and pH depends on type(s) of the component molecules (DNA, PNA, LNA and others) that make up a probe. Probes can incorporate fluorescent labels that make them detectable by fluorescence imaging.

Many different fluorescent labels (fluorophores) have been developed for use in biological assays. There are labels with excitation and emission wavelengths ranging from the ultraviolet to the near-infrared regions of the electromagnetic spectrum. Labels further differ in the width of the excitation and emission bands, the Stokes shift, and the fluorescence lifetime. Representative fluorescent labels include fluorescein, tetramethyl rhodamine, Texas Red, and Cy5.

Fluorescence-in-situ-hybridization (FISH) is an assay utilizing fluorescently labeled probes. In one type of FISH assay, probes directed at ribosomal RNA (rRNA) are used. The sequence of rRNA varies from species to species. This allows FISH assays to be made species-specific through the proper design of the probe sequence. Agents that help to preserve RNA directly such as TCEP and the cationic, quaternary ammonium salts, tetra- and hexa-decyltrimethylammonium bromide, like those found in RNAprotect Bacteria Reagent (Qiagen 76506) or indirectly by maintaining the bacterial cell wall (e.g. Mg504) can be beneficial to these assays. PNA FISH assays are commercially available for diagnostic use in hospital clinical microbiology laboratories for the identification of microorganisms in suspected blood stream infections. In these assays, the probes comprise fluorescently labeled PNA molecules.

The advantage of this second class of assays is that they result in intact cells that can be microscopically examined. This allows the size, shape and clustering characteristics of the cells to be assessed along with the staining behavior. PNA FISH is particularly advantageous because of its generality, high specificity and easily visualized fluorescence.

The third class of assays for the detection and identification of microorganisms encompasses those that involve the use of molecular methods, including amplification techniques such as PCR. In contrast to the first two classes of assays in which the cells to be detected remain intact, in these assays the target is microbial DNA. RNA or proteins that have been released by the lysis or rupture of the cells. In the case of PCR, the product(s) of the amplification can be detected by sequencing, through the use of microarrays, by the use of intercalating dyes or with probes carrying a detectable label such as one or more fluorophores or nanoparticles. Amplification-based methods suffer from certain drawbacks including false negatives due to inhibitors present in many biological samples, and false positives caused by remnant DNA from microorganisms killed by host defense mechanisms.

PREFERRED EMBODIMENTS OF THE INVENTION

Selective ultrasonic lysis of whole blood, concentrated platelets, respiratory secretions, urine, or blood culture for the purpose of microbial detection is carried out by treating the sample with a buffered solution comprised of saponin or Tween-20 and proteinase in a ratio ranging from 1:1 to 1:4; lysing the mixture with focused or planar high-frequency ultrasonic waves; and concentrating the lysed sample via filtration or centrifugation. Detection can then be accomplished by the following additional steps: rinsing the concentrate; probing the rinsed concentrate with fluorescently labeled PNA probes and hybridizing the probes to specific rRNA targets; stringent washing to remove unbound and non-specifically hybridized probe; and analyzing the sample to detect fluorescent microorganisms. These are the preferred protocols.

Reagent Preparation

The lysis solutions were optimized individually for each sample type. Saponin was chosen for the lysis of whole blood and platelets for its superior ability to lyse blood cell membranes while leaving bacterial cells intact. Tween-20 was used in place of saponin for respiratory secretions because the sample was easier to filter after treatment with Tween-20 while still preserving the microorganisms.

Whole Blood and Blood Culture Formulation
1) Add 115 mg saponin from *Quillaja* bark purified to remove low molecular weight contaminants (Sigma S4521) to 10 mL 0.1M sodium phosphate buffer, pH 8.
2) Vortex briefly to dissolve.
3) Add 112.5 Units of Proteinase from *Aspergillus melleus* Type XXIII (Sigma S4032) to the solution.
4) Vortex briefly to dissolve.
5) Filter solution with a 32 mm, polyethersulfone (PES) 0.2 um syringe filter.

Concentrated Platelet Formulation
1) Add 58 mg saponin from *Quillaja* bark purified to remove low molecular weight contaminants (Sigma S4521) to 10 mL 0.1M sodium phosphate buffer, pH 8.

2) Vortex briefly to dissolve.
3) Add 56.25 Units of proteinase from *Aspergillus melleus* Type XXIII (Sigma S4032) to the solution.
4) Vortex briefly to dissolve.
5) Filter solution with a 32 mm PES 0.2 um syringe filter.

Possible perturbations: The concentration of saponin and/or proteinase may be increased to promote filterability or decreased to improve recovery. Additional agents to promote degradation of fibrin clots and filterability such as Streptokinase may be added.

Respiratory Secretions Formulation
1) Add 115 µL of Tween-20 to 10 mL 0.1M sodium phosphate buffer, pH 8.
2) Vortex well to mix completely.
3) Add 112.5 Units of proteinase from *Aspergillus melleus* Type XXIII (Sigma S4032).
4) Vortex briefly to dissolve.
5) Filter solution with a 32 mm PES 0.2 um syringe filter.

Urine Formulation
1) Add 250 µL of Tween-20 to 50 mL of 1× Phosphate Buffered Saline (Sigma P7059).
2) Filter solution with a 32 mm PES 0.2 um syringe filter.

Possible perturbations: Proteinase may be added to this formulation to increase filterability.

Sample Preparation
1) Add 1 mL of lysis solution to a 3 mL round bottom glass tube (Covaris 520067).
2) Add 1 mL of sample: whole blood anti-coagulated with sodium heparin, concentrated platelets anti-coagulated with acid-citrate-dextrose (ACD), or respiratory secretions without preservative.
3) Cap tube (SUN-SRi 200596) and invert to mix several times.

Possible perturbations: 1) 200 µL of Bond Breaker TCEP Solution (Thermo Scientific 77720) may be added to the preparation to protect RNA and/or to improve filterability of respiratory secretions. 2) For very thick, mucoid respiratory secretions or for blood culture with $10^5$ CFU/mL or more less sample may be added to the preparation and the difference in volume may be replaced with additional lysis solution, water, or buffer. 3) Anti-coagulants other than those listed above may be used for whole blood and concentrated platelets.

Ultrasonic Lysis

The sample was treated with acoustic energy to promote mixing, selectively lyse human cells over bacteria and yeast, and break apart sample matrix for improved filtration. This has been done with focused acoustic energy in the Covaris S2 and non-focused acoustic energy with the ProSys.

Covaris method
1) Heat water bath to 37° C. by setting chiller to 37.7° C.
2) Degas water bath for 30 min prior to use per manufacturer's instruction.
3) Place 3 mL glass tube into tube holder (custom-built tube holder with fixed positioning of the tube in the vertical and horizontal axes).
4) Treat sample for 100 seconds at 10% duty cycle, 1 intensity, 1000 cycles/burst
5) Treat sample for 60 seconds at 10% duty cycle, 2 intensity, 1000 cycles/burst
6) Treat sample for 60 seconds at 10% duty cycle, 2 intensity, 200 cycles/burst Possible perturbations: 1) Reduce treatment time in step 5 and 6 to 30 seconds and cycles/burst to 500 in step 5 and to 100 in step 6 to improve recovery in platelets. 2) Treat urine with 3 cycles of step 6 only. 3) Treat blood culture with 1 cycle of step 6 only.

Concentration, Hybridization, and Detection

The lysate was concentrated on an aluminum and $SiO_2$ coated polycarbonate track etched membrane (PCTE) filter bonded to a plastic slide with a ring press and supported by a stainless steel fit. The slide was held in a custom-built, heated slide holder with a vacuum manifold. The filtration area was 52 $mm^2$ Concentration Method
1) Filter entire lysate using a vacuum equivalent 5 to 15 inches of Hg.
2) Rinse filter and holder 3 times with 830 µL each of 1×PBS while vacuuming
3) Turn off and purge vacuum.

Possible perturbations: 1) The lysate may be rinsed with a 1% solution of dextran sulfate, RNAprotect, and/or 400 mM $MgCl_2$ in 1×PBS to improve hybridization and detection. 2) The lysate may be concentrated using centrifugation rather than filtration. 3) Less than the entire volume of lysate may be filtered for samples from which only high colony count organisms are relevant like urine.

Hybridization and Wash Method
1) Filter PNA FISH Flow Hybridization Buffer immediately prior to use with a 13 mm, 0.2 µm, polytetrafluorethylene (PTFE) syringe filter.
2) Add 400 µL of filtered or PNA FISH Flow Hybridization Buffer containing 100 nM to 500 nM or 50 nM probe for bacteria or yeast respectively to the holder.
3) Cover the holder to prevent evaporation.
4) Heat the retentate and hybridization buffer in the holder for 30 minutes at 55° C.
5) Vacuum away hybridization buffer.
6) Turn off and purge vacuum.
7) Add 500 µL of PNA FISH Flow Wash Buffer to the holder.
8) Cover holder to prevent evaporation.
9) Heat the retentate and wash buffer in the holder for 10 minutes at 55° C.
10) Vacuum away wash buffer.
11) Turn off and purge vacuum.
12) Repeat steps 6-10.

Possible perturbations: 1) Add 40 ul of Bond Breaker TCEP Solution to the holder with the hybridization buffer to protect RNA and improve hybridization and detection. 2) Add 10% methanol to the wash buffer to preserve Gram negative cells during wash step. 3) Use Tween-20 in the wash buffer rather than Triton-X to preserve *Streptococcus pneumoniae*. 4) Add 1% solution of dextran sulfate, RNAprotect, and/or 400 mM $MgCl_2$ to the wash buffer improve hybridization and detection.

Detection
1) Remove slide from the holder and allow to air dry.
2) Add 1 drop of mounting media (20% (v/v) 1M Tris-HCl pH 7.6, 80% (v/v) glycerol and 2% (w/v) DABCO) and a 15 mm, round, glass coverslip (Ted Pella, Inc. 26024).
3) View and image filter immediately after adding mounting media on a fluorescent microscope or automated scanner.

Possible perturbations: The concentrated, hybridized lysate may be fixed to and viewed, imaged, and/or scanned on a solid surface rather than a filter.

Mass Spectrometry Analysis

Following lysis, mass spectrometry (MS) can be used for detection, identification, characterization or quantification of microorganisms in a sample.

In an embodiment, the detection, identification, characterization or quantification is done by a mass spectrometer, which may be one of the following: matrix-assisted-laserdesorption-ionization (MALDI) mass spectrometry (e.g. MALDI-TOF MS), Tandem MS, ESI-TOF, ESI-iontrap, LC-MS, GC-MS, ion mobility MS, laser desorption ionization mass spectrometry (LDI-MS) and quadrupole-MS. Other mass spectrometry devices and methods now existing or which may be developed are also within the scope of the present invention.

Mass spectrometry is a sensitive and accurate technique for separating and identifying molecules. Generally, mass spectrometers have two main components, an ion source for the production of ions and a mass-selective analyzer for measuring the mass-to-charge ratio of ions, which is and converted into a measurement of mass for these ions. Several ionization methods are known in the art and described herein.

Different mass spectrometry methods, for example, quadrupole mass spectrometry, ion trap mass spectrometry, time-of-flight mass spectrometry, gas chromatography mass spectrometry and tandem mass spectrometry, can utilize various combinations of ion sources and mass analyzers which allows for flexibility in designing customized detection protocols. In addition, mass spectrometers can be programmed to transmit all ions from the ion source into the mass spectrometer either sequentially or at the same time. Furthermore, a mass spectrometer can be programmed to select ions of a particular mass for transmission into the mass spectrometer while blocking other ions.

Mass spectrometers can resolve ions with small mass differences and measure the mass of ions with a high degree of accuracy. The high degree of resolution and mass accuracy achieved using mass spectrometry methods allows the use of large sets of tagged probes because the resulting reporter tags can be distinguished from each other. The ability to use large sets of tagged probes is an advantage when designing multiplex experiments.

Another advantage of using mass spectrometry is based on the high sensitivity of this type of mass analysis. Mass spectrometers achieve high sensitivity by utilizing a large portion of the ions that are formed by the ion source and efficiently transmitting these ions through the mass analyzer to the detector. Because of this high level of sensitivity, even limited amounts of sample can be measured using mass spectrometry.

Mass spectrometry methods are well known in the art (see Burlingame et al. Anal. Chem. 70:647 R-716R (1998); Kinter and Sherman, Protein Sequencing and Identification Using Tandem Mass Spectrometry Wiley-Interscience, New York (2000)).

In recent years, MALDI-TOF mass spectrometry has emerged as a powerful tool for the identification of bacteria and other microorganisms. The advantages of this approach include relatively straightforward sample preparation and rapid analysis. Intact bacterial cells from, for example, a colony can be mixed with MALDI matrix and applied directly to the MALDI sample plate. Pattern recognition applied to the complex spectra that are obtained allows identification of bacteria, often to the strain level (see Lay. Mass Spectrometry Reviews 20: 172-194 (2001)).

Mass spectrometry and MALDI-TOF in particular is well suited for the analysis of microorganisms obtained using the methods of the invention.

EXAMPLES

The examples below demonstrate the methods for clinical samples such as blood, platelet concentrates and bronchoalveolar lavage. The method will have utility for many other types of samples in which the detection of microorganisms at low levels is of value. These include biological samples such as tissue, stool, lavage fluids, needle aspirates and saliva. Another category includes foods such as milk, meats, cheese and vegetables.

Example 1 Filterability Comparison of the Selective Ultrasonic Lysis Approach with the Zierdt Method Whole, sodium heparin anti-coagulated blood was mixed 1:1 or 1:10 with a lysis solution based on Zierdt's refined lysis solution (Zierdt, J. Clin. Microbiol., 1982) which contained Rhozyme 41 (Rohm and Hass, Philadelphia, Pa.), a crude proteinase mixture extracted from *Aspergillus oryzae* and Tween-20 in sodium phosphate buffer. Rhozyme 41 was no longer available; proteinase from *Aspergillus melleus* was substituted. The mixtures of blood and lysis solution were subjected to one hour incubation at 37° C., focused ultrasonic waves in the Covaris, or no treatment. Then they were tested for filterability and examined microscopically to assess the number of residual cells.

Two lysis solutions were made—one with and one without detergent. The lysis solutions were made by adding 350 µL of Tween-20 to 49.65 mL of 0.01 M sodium phosphate buffer and mixing thoroughly. Then, if required, 250 mg of proteinase were added and briefly vortexed to dissolve. Lysis solutions were filtered with a 0.2 µm, 32 mm, PES syringe filter.

Samples were prepared by adding 0.5 mL of whole blood and 0.5 mL of lysis solution (1:1) to a 2 mL, round-bottom, snap-cap, plastic microcentrifuge tube (Eppendorf 022363352) or 0.1 mL of blood and 0.9 mL of lysis solution (1:10). The samples were capped and inverted to mix. The samples remained at these concentrations during the incubation at 37° C. or treatment with the Covaris. The 1:1 sample was diluted 1:5 before being examined microscopically or tested for filterability in order to obtain the same blood to fluid ratio as the 1:10 samples.

Samples were heated in a 37° C. water bath for one hour in accordance with Zierdt's lysis procedure (Zierdt, J. Clin. Microbiol., 1982). Other samples were treated with the Covaris S2 instead of heat. The Covaris bath was filled with deionized water, degassed for 30 minutes, and chilled to 7° C. to promote better sound transmission according to the manufacturer's recommendations. The Covaris bath was not chilled for all of the testing in order to promote proteinase activity. When the bath was not chilled it reached 25° C. The Covaris samples were treated for 60 consecutive seconds at an intensity of 3, 10% duty cycle, and 200 cycles per burst. Control samples were mixed with lysis solution and tested immediately after mixing.

All samples were examined for residual cells using bright field microscopy and a 20x objective. Slides were made by pipetting 15 µL of thoroughly mixed sample (1:10) onto a glass slide and adding a 22x22 mm coverslip. An average number of cells was taken over multiple fields of view.

All samples were tested for filterability as a measure of how well the cells had been lysed. The barrel from a 3 mL syringe was fitted with a 13 mm, 0.45 µm, nylon syringe filter. The outlet of the syringe filter was attached to a vacuum pulling at 5" Hg. The filter was primed with 0.5 mL of 1xPBS. Another 1 mL of 1xPBS was filtered and timed to obtain a normalization value for each filter. Finally 1 mL of sample mixed with lysis solution and either treated with heat or sonic energy or untreated was filtered and timed.

TABLE 1

Filterability and Microscopic Appearance of Whole
Blood Following Various Lytic Treatments

| Blood:Lysis Solution | Lysis Solution and Treatment | Microscopy (cells/20X field) | Filtration (sec) |
|---|---|---|---|
| 1:10 | Detergent | 25 | ∞ |
| | Detergent & proteinase | 75 | 27 |
| | Detergent & proteinase for 1 hr @ 37° C. (Zierdt method) | 1 | 23 |
| | Detergent with Covaris @ 7° C. | 0 | 15 |
| | Detergent & proteinase with Covaris @ 25° C. | 0 | 14 |
| 1:1 | Detergent & proteinase for 1 hr @ 37° C. | Not tested in this experiment; this does not filter | |
| | Detergent with Covaris @ 7° C. | 12-18 | 61 |
| | Detergent & proteinase with Covaris @ 25° C. | 12-18 | 15 |

Results showed that treatment with ultrasonic energy produced a lysate that was more filterable and contained less cellular debris than the Zierdt method (Table 1). Although not tested during these experiments, other work showed the Zierdt method produced a product that was not filterable if used in a 1:1 mixture with whole blood. They also demonstrated that the composition of the lysis fluid has secondary contributions to filterability. However, it was unclear whether the significant gain in filterability for the 1:1 sample with detergent and proteinase over the sample with detergent only was due to the proteinase or the warmer Covaris bath. Further experiments were conducted at the same temperature. The results showed adding proteinase to the ultrasonic lysis increases filterability and may also reduce the number of residual blood cells even though the sonic treatment only lasted 60 seconds and it was at room temperature (Table 2). This indicates that the acoustic energy may have been speeding up enzymatic reactions as well as shearing cells.

TABLE 2

Filterability and Microscopic Appearance of Whole
Blood Treated with Proteinase and Ultrasonic Energy

| Blood:Lysis Solution | Lysis Solution and Treatment | Microscopy (cells/20X field) | Filtration (sec) |
|---|---|---|---|
| 1:1 | Detergent with Covaris @ 20° C. | 10 | 38 |
| | Detergent & proteinase with Covaris @ 20° C. | 2-3 | 20 |

International patent application WO 2009/015484 A1 (Peytavi et al.) demonstrates the concentration of microbial cells from whole blood using high concentrations of heat-treated saponin and centrifugation. 10% heat-treated saponin in the lysis solution with proteinase and Covaris treatment did not improve filterability (Table 3).

TABLE 3

Filterability of Whole Blood Treated with High
Concentration Saponin and Ultrasonic Energy

| Saponin Concentration in Lysis Solution | Filtration (sec) |
|---|---|
| 10%, heat-treated | 69 |
| 1.4%, untreated | 51 |
| 0.7%, untreated | 56 |

Example 2 Recovery of Microorganisms from Whole Blood after Selective Lysis with Focused Acoustic Energy Nine different microorganisms were inoculated into whole, sodium heparin treated blood. The blood was mixed with lysis solution and plated before and after ultrasonic lysis. The plates were incubated overnight and colonies were counted in the morning to determine percent yield after Covaris treatment in blood and lysis solution.

Candida albicans, Candida krusei, Enterococcus faecium, Enterococcus faecalis, Escherichia coli, Klebsiella pneumoniae, Pseudomonas aeruginosa, Staphylococcus aureus, and Staphylococcus epidermidis were subcultured to non-selective agar media. The plates were incubated at 37° C. overnight. The following morning they were inoculated to broth media from the freshly subcultured agar media and allowed to incubate at 37° C. for 2.5 hours. Bacteria and yeast were diluted serially with 1×PBS with 0.05% Tween-20 to 1:1,000 or 1:10,000.

Lysis solution was made by adding 350 µL of Tween-20 to 49.65 mL of 0.01M sodium phosphate buffer and mixing thoroughly. Then 250 mg of proteinase were added and briefly vortexed to dissolve. The lysis solution was filtered with a 0.2 µm, 32 mm, PES syringe filter.

Samples were prepared by adding 0.5 mL of whole blood, 0.5 mL of lysis solution, and 10 to 40 µL of the diluted microorganisms to a 2 mL, round-bottom, snap-cap, plastic microcentrifuge tube. The samples were capped and inverted to mix. 100 µL of the blood mixture were plated using a plate spinner and a disposable, sterile T-spreader before and after treatment with the Covaris. The plates were incubated overnight at 37° C. overnight. Colonies were counted and recorded the following morning to determine percent yield (Table 4). This experiment was performed three times.

Samples were treated with the Covaris S2. The Covaris bath was filled with deionized water and degassed for 30 minutes. The water bath was maintained at 20° C. The Covaris samples were treated for 60 consecutive seconds at an intensity of 2, 10% duty cycle, and 200 cycles per burst.

TABLE 4

Recovery from Whole Blood after Ultrasonic Lysis

| | Yield | | | | |
|---|---|---|---|---|---|
| Organism | Experiment 1 | Experiment 2 | Experiment 3 | Average Yield | Standard Deviation |
| C. albicans | 300% | 263% | 243% | 268% | 29 |
| C. krusei | 63% | 217% | 129% | 136% | 77 |
| E. faecium | 92% | 134% | 267% | 164% | 91 |
| E. faecalis | 150% | 123% | 165% | 146% | 21 |
| E. coli | 88% | 61% | 63% | 70% | 15 |
| K. pneumoniae | 93% | 41% | 50% | 61% | 28 |
| P. aeruginosa | 41% | 56% | 48% | 48% | 8 |
| S. aureus | 171% | 164% | 143% | 159% | 15 |
| S. epidermidis | 93% | 70% | 192% | 118% | 65 |

The results showed some yields were greater than 100%. In this experiment, the microorganisms were quantitated by the number of colonies formed after overnight growth. Cells in a cluster or chain form single colonies and thus represent single colony forming units (cfu). If disrupted, such clusters can form multiple colonies. We have observed that immediately following treatment with the Covaris, organisms that normally occur in clusters are generally seen to be present in single cell form.

The results also indicated some loss of viability. The impact was greatest on Gram negative rods.

Example 3 Detection of *Staphylococcus aureus* from Selective Lysis of Whole Blood Versus Routine Blood Culture

*Staphylococcus aureus* (SA) that had been diluted serially was inoculated into sterile, fresh, whole, sodium heparin treated blood and incubated to allow for phagocytosis. The blood was then split into two samples and subjected to either selective lysis or turned into a mock blood culture. The portion that underwent selective lysis was filtered. The filter was placed on an agar plate and incubated overnight. Colonies were counted in the morning. The portion that was made into a mock blood culture was incubated two days and checked for growth using Gram stain and subculture to an agar plate. The results of both methods were compared to the number of CFU initially inoculated into the blood and to each other.

SA (ATCC 29213) was subcultured to trypticase soy agar with 5% sheep blood and incubated at 37° C. overnight. The following morning it was inoculated into trypticase soy broth and incubated at 37° C. at 180 rpm for 2 hours. The broth was then diluted serially 1:10 with 1× phosphate buffered saline with 0.05% Tween-20 to $1\times10^{-9}$. 100 µl of the $10^{-5}$ and $10^{-6}$ dilutions and 1 mL of the $10^{-7}$, $10^{-8}$, and $10^{-9}$ dilutions were filtered with the Microfil V Filtration Device (Millipore MVHAWG124) that had been pre-wetted with 1× phosphate buffered saline. The device contains a 47 mm, mixed cellulose ester filter with 0.45 µm pores and a printed grid for counting colonies. The filter was removed from the device, placed on trypticase soy agar, and incubated overnight at 30° C. The filters were examined for growth the following morning, and colonies were counted. These counts were used to estimate how many CFU were added to the aliquots of blood.

The lysis solution was prepared by adding 140 mg of saponin to 10 mL of 0.1M sodium phosphate buffer, pH 8 and vortexing to dissolve. Then 51 mg of proteinase were added and vortexed briefly to dissolve. The solution was filtered with a 0.2 µL, 32 mm, PES syringe filter.

Five 2.5 mL aliquots of blood were inoculated with 50 µL each of the last five SA dilutions, $10^{-5}$ to $10^{-9}$, and incubated for 1 hour at 37° C. to allow for phagocytosis. The samples were then mixed and split into separate 1 mL aliquots. The excess 0.55 mL from each sample was discarded. Each 1 mL aliquot was either mixed with 1 mL of lysis solution or 3 mL of BacT/ALERT SA blood culture media (Biomérieux 259789).

The mock blood cultures were incubated for 2 days at 37° C. and 180 rpm. They were Gram stained and subcultured semi-quantitatively to trypticase soy agar each morning to monitor for growth. The agar subcultures were incubated overnight at 37° C. and examined for growth the following morning.

The bath on the Covaris was filled with deionized water, heated to 37° C., and degassed for 30 minutes. The aliquots that were mixed with lysis solution were loaded into the custom tube holder designed to fix the X and Y axis. The samples were warmed and mixed for 100 seconds at an intensity of 1, 10% duty cycle, and 1000 cycles per burst. Then the intensity was increased to 2 for 60 seconds. Finally, the cycles per burst were decreased to 200 for 60 seconds.

The lysed samples were filtered on Microfil V filtration devices that had been pre-wetted with 1× phosphate buffered saline. The filters were rinsed with more 1× phosphate buffered saline. The filters were removed from the device, placed on trypticase soy agar, and incubated overnight at 30° C. The filters were examined for growth the following morning, and colonies were counted.

TABLE 5

Comparison of Selective Lysis of Whole Blood and Blood Culture

| Approx. CFU Added to Each Split Sample | Number of Colonies from Selectively Lysed Whole Blood on Day 1 | Growth or No Growth of Blood Culture |
|---|---|---|
| 64.6 | 159 | Growth Day 1 |
| 6.8 | 37 | Growth Day 1 |
| 0.56 | 0 | No Growth Day 2 |
| 0.04 | 0 | No Growth Day 2 |
| 0 | 0 | No Growth Day 2 |

The data demonstrate that selective lysis of whole blood for the detection of SA was as sensitive as blood culture. Selective lysis, however, has the advantage that isolated colonies were available for analysis after overnight incubation; whereas, the blood culture would require another overnight incubation before overnight colonies were available (Table 5).

Example 4 Detection of Coagulase-Negative *Staphylococcus* from Clinical, Whole Blood Samples Four leftover clinical samples of ethylenediaminetetraacetic acid (EDTA) anti-coagulated whole blood from suspected catheter-related blood stream infections (CR-BSI), reported clinically as $10^6$ cfu/mL Coagulase Negative *Staphylococcus* (CNS), were received frozen. They were defrosted, mixed with lysis solution, treated with focused ultrasonic energy, and filter concentrated. The retentate was probed using the PNA Flow FISH method on the membrane and examined using fluorescent microscopy.

Lysis solution was prepared by adding 115 mg of saponin to 10 mL of 0.1M sodium phosphate buffer, pH 8 and vortexing to dissolve. 11.25 Units/mL of proteinase were added and vortexed briefly to dissolve. The solution was filtered using a 0.2 µm, 32 mm, PES syringe filter.

Samples were prepared by adding 1 mL of lysis solution and 1 mL of defrosted blood to a 3 mL, round bottom, glass Covaris tube. The samples were mixed by inversion.

The bath on the Covaris was filled with deionized water, heated to 37° C., and degassed for 30 minutes. The tubes were loaded into the custom tube holder designed to fix the X and Y axis. The samples were warmed and mixed for 100 seconds at an intensity of 1, 10% duty cycle, and 1000 cycles per burst. Then the intensity was increased to 2 for 60 seconds. Finally, the cycles per burst were decreased to 200 for 60 seconds.

The lysed samples were filter-concentrated, hybridized, washed, and mounted as described in the Preferred Embodiments section. The retentate was probed with a three probe mixture containing a *S. aureus* specific, fluorescein-labeled probe, a CNS specific, TAMRA-labeled probe, and universal bacteria, Cy5-labeled probe.

Figure 1:
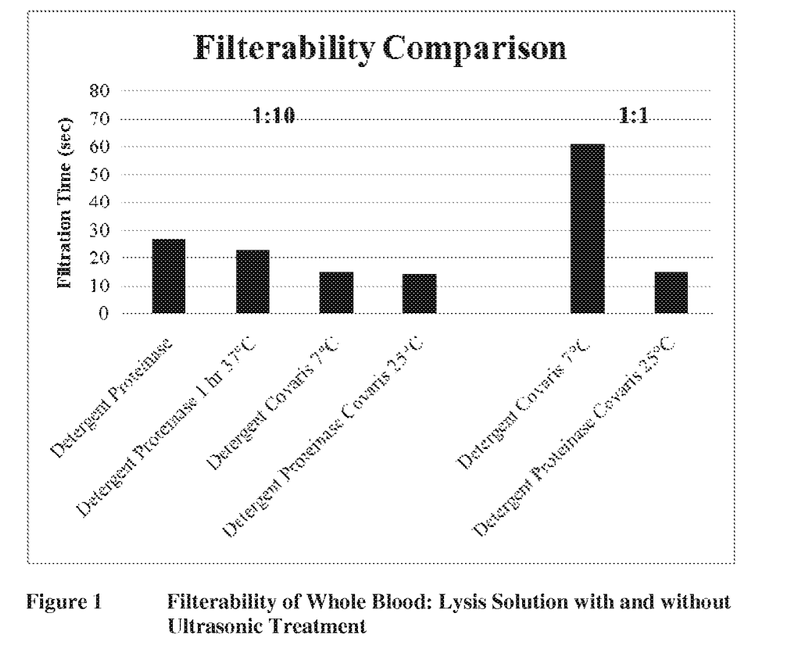
FIG. 1 is a graph that shows the filterability of whole blood: lysis solution with and without ultrasonic treatment.
Figure 2:
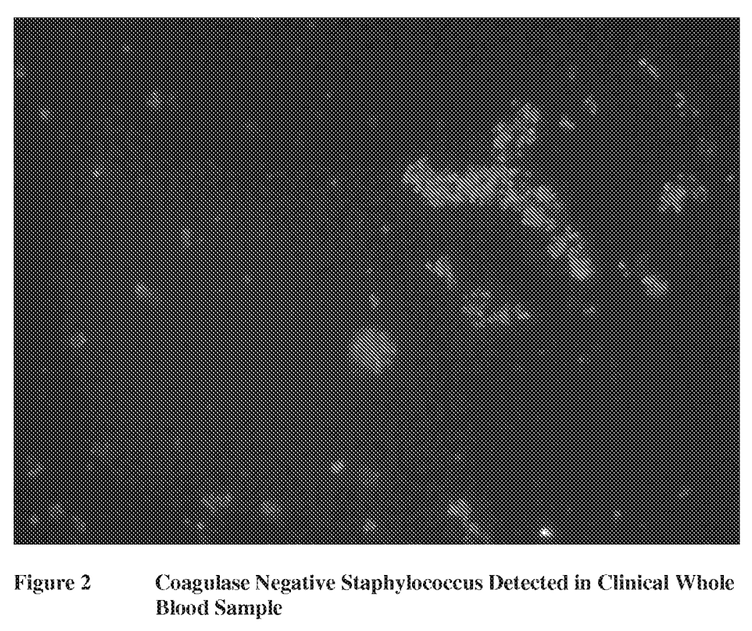
FIG. 2 shows the results of Fluorescence in situ Hybridization (FISH) experiments for Coagulase Negative *Staphylococcus* (CNS). The slide-bound membranes were examined using a fluorescent microscope, a 60× oil objective, and the AdvanDx PNA FISH filter cube (XF 53) for fluorescent organisms. CNS was detected in all 4 samples.

The slide-bound membranes were examined using a fluorescent microscope, a 60× oil objective, and the AdvanDx PNA FISH filter cube (XF 53) for fluorescent organisms. CNS was detected in all 4 samples (FIG. 2).

Example 5 Whole Blood Lysis with Non-Focused Acoustic Energy

Whole blood anti-coagulated with sodium heparin was inoculated with *E. coli*, mixed with lysis solution and subjected to non-focused ultrasound from the ProSys megasonic bowl instrument. Samples were plated before and after treatment with the ProSys to determine recovery and tested for filterability.

An adjustable tube holder for the ProSys megasonic bowl was devised by attaching a clip to a manual positioning stage of the kind used for optics prototyping. The tool clip was kept level to keep the sample parallel to the transducer surface. The positioning stage allowed the height of the tube to be precisely adjusted in order to maximize the amount of activity within the sample while it was being treated with the ProSys. The ProSys bowl was filled with deionized water. The transducer was used to heat the water in the bowl until it reached 35° C.

Lysis solution was made by adding 115 mg of saponin to 10 mL of 0.1 M sodium phosphate buffer and vortexing to dissolve. Then 112.5 units of proteinase were added and briefly vortexed to dissolve. The lysis solution was filtered with a 0.2 µm, 32 mm, PES syringe filter.

Samples were prepared by adding 1 mL of whole blood and 1 mL of lysis solution to a 15 mL Falcon tube. The tubes were sealed with a cyclic-olefin polymer (COP), pressure-sensitive adhesive tape (Adhesives Research, ARseal 90404) and mixed by inversion.

The tubes were clipped topside down to the tube holder and lowered into the bath until fully submerged. They were treated with the ProSys for 5 consecutive minutes with 45 watts, 100 ms pulse, and 50% duty cycle. The temperature was maintained in the bowl between 36° C. and 38° C. by removing warm water and replacing it with icy, deionized water. The lysate was removed from the tube holder and tested for filterability as described in Example 1. Identical samples were subjected to focused sonic lysis by the Covaris in parallel with the ProSys samples for comparison (Table 6). This experiment was performed four times.

TABLE 6

Comparison of ProSys and Covaris Whole Blood Lysate Filterability

| Experiment | Ultrasonic System | Filtration (sec) |
|---|---|---|
| 1 | ProSys | 55 |
| 1 | ProSys | 60 |
| 1 | ProSys | 46 |
| 1 | ProSys | 62 |
| 1 | Covaris | 57 |
| 2 | ProSys | 63 |
| 2 | ProSys | 63 |
| 2 | ProSys | 70 |
| 2 | Covaris | 56 |
| 3 | ProSys | 40 |
| 3 | ProSys | 44 |
| 3 | ProSys | 43 |
| 3 | ProSys | 50 |
| 3 | Covaris | 52 |
| 4 | ProSys | 46 |
| 4 | ProSys | 47 |
| 4 | ProSys | 46 |
| 4 | ProSys | 60 |
| 4 | Covaris | 55 |

The results showed that the lysis produced by the non-focused acoustic energy from the ProSys compared favorably to the focused ultrasonic energy from the Covaris. The results also indicate that the lysis can be done reliably and reproducibly. Recovery assays were done with *E. coli* to test whether lysis caused by the ProSys was selective for blood cells.

*Escherichia coli* was subcultured to a trypticase soy agar (TSA) plate and incubated at 37° C. overnight. The following morning it was inoculated to trypticase soy broth (TSB) media from the freshly subcultured plate and allowed to incubate at 37° C. for 2 hours. 350 µL of sterile broth were added to 600 µL of broth culture. The *E. coli* were further diluted serially with 1×PBS with 0.05% Tween-20 to 1:10,000. 20 µL of diluted culture were added to samples prepared as described above.

100 µL of the samples were plated before and after treatment with the ProSys (as described above) using a plate spinner and a disposable, sterile T-spreader. The plates were incubated overnight at 37° C. Colonies were counted and recorded the following morning to determine percent yield. Identical samples were subjected to focused sonic lysis by the Covaris in parallel with the ProSys samples for comparison (Table 7).

TABLE 7

*E. coli* Recovery from Whole Blood after Lysis with the ProSys

| Ultrasonic System | CFU Pre-Lysis | CFU Post-Lysis | Yield |
|---|---|---|---|
| ProSys | 29 | 11 | 38% |
| ProSys | 25 | 17 | 68% |
| ProSys | 32 | 12 | 38% |
| ProSys | 20 | 13 | 65% |
| Covaris | 28 | 15 | 54% |

The recovery results for lysis with the ProSys compared favorably to the Covaris.

Example 6 Detection of Bacteria in Concentrated Platelets

Platelets from one unit of blood (450 mL) were separated and concentrated in approximately 30 mL of plasma by centrifugation. 1 mL aliquots of platelet concentrate were inoculated with bacteria, mixed 1:1 with lysis solution, and selectively lysed using the Covaris S2. The lysates were filtered, and the retentates were probed with fluorescently labeled universal bacteria PNA probe. The filters were examined on a fluorescent microscope for the presence of bacteria. The platelets were plated pre- and post-lysis to determine the detection limits of this invention.

The platelets were stored on a rotational shaker (Manufacturer: VWR, Model: S-500 Orbital Shaker) at ambient temperature. The speed of oscillation was set between 3 and 4 such that an overall speed of 70 rotations per minute was achieved. Platelets were extracted from the bag in a laminar flow hood using aseptic technique.

Lysis solution was prepared daily. 115 mg of saponin were added to 10 mL of 0.1 M sodium phosphate buffer, pH 8.0 and mixed to homogeneity via gentle shaking and inversion. 37 mg of proteinase were added and mixed gently to avoid foaming (foaming indicates possible denaturation of protein). The lysis solution was filtered with a 32 mm, 0.2 µm, PES syringe filter. The tube was protected from light to prevent degradation of the enzyme.

*Serratia marcescens* (ATCC 14756), *Enterobacter cloacae* (ATCC 13047), *Salmonella choleraesuis* (ATCC 10708), *Salmonella enteritidis* (NCTC 4444), *Escherichia coli* (ATCC 35218), *Klebsiella pneumoniae* (ATCC 13882), *Pseudomonas aeruginosa* (10145), *Staphylococcus aureus* (ATCC 29213), *Staphylococcus epidermidis* (14990), *Streptococcus agalactiae* (ATCC 13813), *Propionibacterium acnes* (ATCC 11827), *Bacillus cereus* (ATCC 10876) were subcultured to non-selective agar media. The plates were incubated at 37° C. overnight or at room temperature for 3 days. The following morning they were inoculated to TSB from the freshly subcultured agar media and allowed to incubate at 37° C. for 2 to 4 hours. *P. acnes* was grown for 1 to 2 days. Broth cultures were diluted 1:10 serially with sterile broth to 1:1,000,000. $10^{-3}$ to $10^{-6}$ were the four dilutions used for testing.

Samples were prepared by mixing 1.1 mL, of concentrated platelets and 100 μL of diluted bacteria in a 3 mL, glass, round-bottom Covaris tube. Two 100 uL aliquots were removed for plating. 1 mL of lysis solution was added to the inoculated platelets. The Covaris tubes were capped and inverted to mix. 200 uL of TCEP were added to platelet solution; and the contents of the Covaris tubes were pipetted vigorously to ensure complete mixing of the sample and to dissociate the gel-like residue that is generated upon addition of TCEP to platelets. The two 100 μL aliquots (replicates) from the inoculated platelets were plated using a plate spinner and disposable T-spreaders. After incubation the colonies were counted, and the number of CFU/mL added to the platelets was determined.

The bath on the Covaris was filled with deionized water, heated to 37° C., and degassed for 30 minutes. The tubes were loaded into the custom tube holder designed to precisely position the tube. Each sample was processed via the Covaris to accelerate the lysis of platelets. The samples were warmed and mixed for 100 seconds at an intensity of 1, 10% duty cycle, and 1000 cycles per burst. For the next 30 seconds, the intensity was set to 2 and the cycles per burst was set to 500. For the final 30 seconds, the cycles per burst was set to 100.

The lysate was filter-concentrated, hybridized, washed, and mounted as described in the Preferred Embodiments section. It was probed with a TAMRA-labeled universal bacteria PNA probe. Gram positive specimens were prepared using 1× lysis solution. Gram negative samples were prepared using ½× lysis solution with 200 uL TCEP and 10% methanol (v/v) flow wash buffer. The gram negative protocol also worked on gram positives with the same efficacy.

Figure 3:
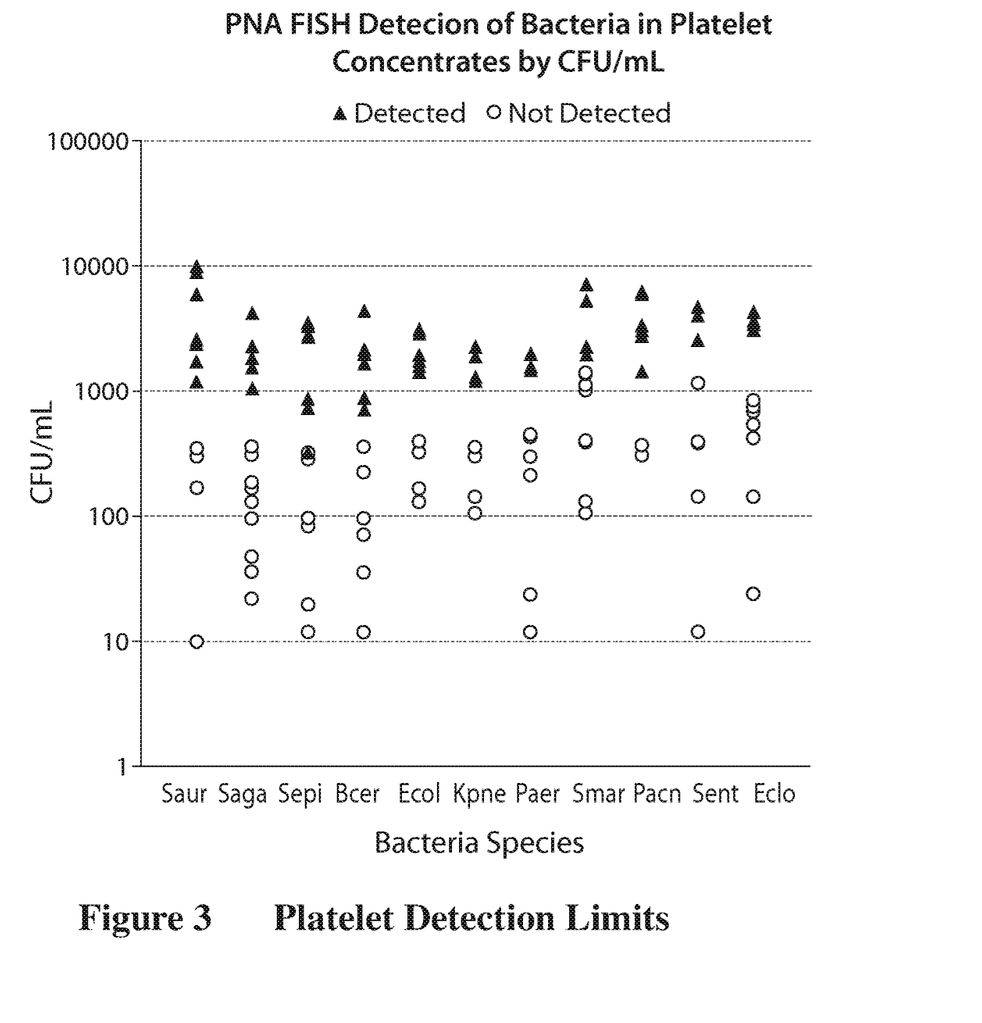
FIG. 3 is a graph that shows peptide nucleic acid (PNA) FISH detection of bacteria in platelet concentrates by CFU/mL.
Figure 4:
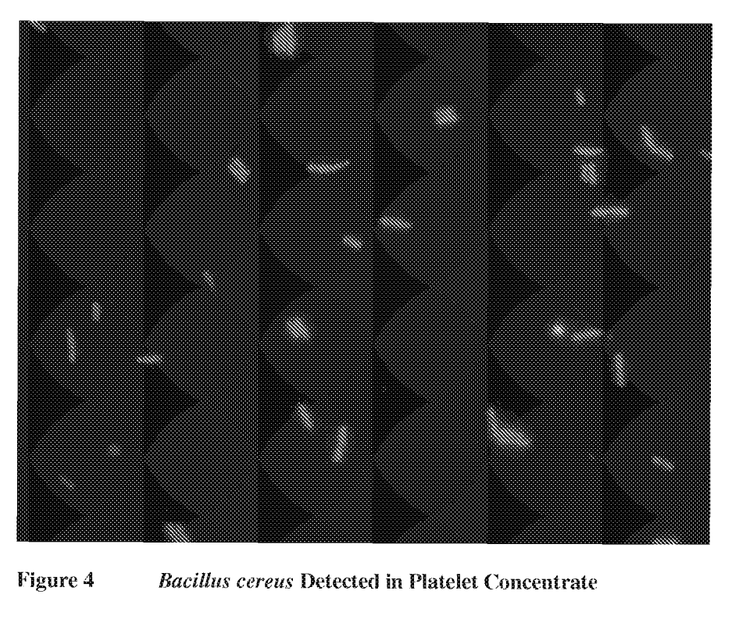
FIG. 4 shows the results of FISH experiments for the detection of *Bacillus cereus* in concentrated platelets.

The slide-bound membranes were examined on the fluorescent microscope using the 60× oil objective and the AdvanDx PNA FISH filter cube (XF 53). The goal was to determine which was the most dilute sample with detectable, fluorescent organisms on the membrane in order to establish the lower limit of detection (FIGS. 3 & 4). The results showed that all of the isolates were detectable between 1000 CFU/mL and 10,000 CFU/mL, and *S. epidermidis* was detectable between 100 CFU/mL and 1,000 CFU/mL by the method of this invention.

Example 7 Filterability of Bronchoalveolar Lavage

Large volume or pooled leftover clinical samples of bronchoalveolar lavage (BAL) were obtained from a hospital laboratory. They were mixed with different processing solutions, treated with the Covaris to break apart mucous, debris, and cells, and tested for filterability.

Samples were prepared by homogenizing large volume or pooled BAL with forceful pipetting and vortexing. 0.5 mL to 1 mL of sample was mixed by inversion and vortexing with 1 mL to 1.5 mL of processing solution in a 3 mL round-bottom, glass Covaris tube.

The bath on the Covaris was filled with deionized water, heated to 37° C., and degassed for 30 minutes. The tubes were loaded into the custom tube holder designed to precisely position the tube. The samples were warmed and mixed for 100 seconds at an intensity of 1, 10% duty cycle, and 1000 cycles per burst. For the next 60 seconds, the intensity was set to 2. For the final 60 seconds, the cycles per burst was set to 200.

All samples were tested for filterability as a measure of how well the BAL had been processed. The barrel from a 3 mL syringe was fitted with a 13 mm, 0.45 μm, nylon syringe filter. The outlet of the syringe filter was attached to a vacuum pulling at 5" Hg. The filter was primed with 0.5 mL of 1×PBS. Another 1 mL of 1×PBS was filtered and timed to obtain a normalization value for each filter. Finally 2 mL of sample mixed with processing solution either treated with sonic energy or untreated was filtered and timed (Table 8).

TABLE 8

Development of BAL Processing Solution

| Processing Solution | % Filtered Before Clogging | Filtration (sec) |
|---|---|---|
| 0.5 mL BAL + 1.5 mL solution (pooled BAL #8-11) | | |
| Sodium Phosphate Buffer | 10 | n/a |
| Sodium Phosphate Buffer + Covaris | 33 | n/a |
| Saponin + Covaris | 70 | n/a |
| Saponin + DNase + Covaris | 100 | 161 |
| DNase + Covaris | 20 | n/a |
| Triton X-100 + Covaris | 100 | 36 |
| Guanidinium Cl + Covaris | 50 | n/a |
| Sputolysin + Covaris | 25 | n/a |
| NaLC + Sodium Citrate + Covaris | 40 | n/a |
| TCEP + Covaris | 40 | n/a |
| 1 mL BAL + 1 mL solution (pooled BAL #8-11) | | |
| Triton X-100 + Covaris | 45 | n/a |
| 1 mL BAL + 1 mL solution (large volume BAL # 12) | | |
| Sodium Phosphate Buffer | 15 | n/a |
| Sodium Phosphate Buffer + Covaris | 30 | n/a |
| Triton + Protease + Covaris | 100 | 26 |
| Triton X-100 + Covaris | 50 | n/a |
| Triton + Protease + DNase + Covaris | 100 | 40 |
| Triton + DNase + Covaris | 100 | 63 |
| Guanidinium + Triton + Covaris | 100 | 33 |
| NaLC + Sodium Citrate + Triton + Covaris | 100 | 76 |
| Triton + Protease + DNase + Guanidinium + Covaris | 100 | 29 |
| Triton + Protease + DNase + NaLC + Covaris | 100 | 35 |
| Repeat Triton + Protease + Covaris | 100 | 28 |
| Repeat Triton + Protease + DNase + Covaris | 100 | 39 |
| 1 mL BAL + 1 mL solution (large volume BAL # 14) | | |
| Sodium Phosphate Buffer | 5 | n/a |
| Sodium Phosphate Buffer + Covaris | 10 | n/a |
| Mucolexx + Covaris | 10 | n/a |
| Triton + Protease + NaLC + Covaris | 55 | n/a |
| Triton + Protease + NALC + NaCitrate + Covaris | 45 | n/a |
| Triton + Protease + Guanidinium + Covaris | 100 | 140 |
| Triton + Protease + Covaris | 30 | n/a |

TABLE 8-continued

Development of BAL Processing Solution

| Processing Solution | % Filtered Before Clogging | Filtration (sec) |
|---|---|---|
| Triton + Protease + TCEP + Covaris | 100 | 35 |
| Triton + Protease + NALC + DNase + Covaris | 30 | n/a |
| Triton + Protease + NALC + DNase in Running Buffer + Covaris | 55 | n/a |
| Triton + Protease + TCEP + DNase in Running Buffer + Covaris | 100 | 69 |
| 1 mL BAL + 1 mL solution (large volume BAL # 17) | | |
| Sodium Phosphate Buffer | 10 | n/a |
| Sodium Phosphate Buffer + Covaris | 18 | n/a |
| Triton + Protease + Covaris | 45 | n/a |
| Triton + Protease + TCEP + DNase in Running Buffer + Covaris | 100 | 43 |
| Triton + Protease + TCEP + Covaris | 100 | 26 |

Results showed that a processing solution with Triton X 100, proteinase, and TCEP followed by treatment with the Covaris produced the most reliably filterable sample. Others additives such as DNase may or may not improve the efficacy of the processing solution. However, there was some concern about the harmful effects that Triton X 100 may have on bacteria so some alternatives to Triton X 100 were also tested (Table 9).

TABLE 9

Triton X 100 Alternatives for BAL Processing Solution

| Processing Solution | % Filtered Before Clogging | Filtration (sec) |
|---|---|---|
| 0.5 mL BAL + 1.5 mL solution (pooled BAL #64-66) | | |
| NaCl + Protease + TCEP + Covaris | 100 | 32 |
| DexS04 + Protease + TCEP + Covaris | 100 | 42 |
| SDS + Protease + TCEP + Covaris | 100 | 24 |
| Triton + Protease + TCEP + Covaris | 100 | 30 |
| Saponin + Protease + TCEP + Covaris | 100 | 28 |
| Tween-20 + Protease + TCEP + Covaris | 100 | 29 |
| 1 mL BAL + 1 mL solution (pooled BAL #67-68) | | |
| Saponin + Protease + TCEP + Covaris | 18 | n/a |
| Saponin + Protease + TCEP + Covaris | 26 | n/a |
| Saponin + Protease + TCEP + High [DNase] + Covaris | 14 | n/a |
| Saponin + Protease + TCEP + Low [DNase] + Covaris | 16 | n/a |
| Saponin + Protease + TCEP + High [Gelsolin] + Covaris | 22 | n/a |
| Saponin + Protease + TCEP + Low [Gelsolin] + Covaris | 26 | n/a |
| 0.5 mL BAL + 1.5 mL solution (pooled BAL #67-68) | | |
| Saponin + Protease + TCEP + Covaris | 82 | n/a |
| Tween-20 + Protease + TCEP + Covaris | 100 | 35 |
| Saponin + Tween-20 + Protease + TCEP + Covaris | 100 | 73 |

Results showed that Tween-20 along with proteinase, and TCEP followed by ultrasonic treatment was a promising alternative to Triton X 100 in the processing solution for BAL.

Example 8 Detection of Bacteria from Clinical Bronchoalveolar Lavage Samples

Leftover positive clinical BAL samples (BAL #18 and #43 clinical reports: "few *Staphylococcus aureus* and Usual throat organism" and "≥10K cfu/mL *Serratia marcescens*" respectively) were mixed with processing solution, treated with focused ultrasonic energy, and filter concentrated. The retentate was probed using the PNA Flow FISH method on the membrane and examined using fluorescent microscopy.

Processing solution was prepared by adding 115 μL of Triton X 100 to 10 mL of 0.1M sodium phosphate buffer, pH 8 and vortexing to mix thoroughly. 11.25 Units/mL of proteinase were added and vortexed briefly to dissolve. The solution was filtered using a 0.2 μm, 32 mm, PES syringe filter.

Samples were prepared by homogenizing with forceful pipetting and vortexing. 1 mL of processing solution, 1 mL of homogenized BAL, and 0.2 mL of TCEP were added to a 3 mL, round bottom, glass Covaris tube. The samples were mixed by inversion and vortexing until uniformly liquid throughout.

The bath on the Covaris was filled with deionized water, heated to 37° C., and degassed for 30 minutes. The tubes were loaded into the custom tube holder designed to fix the X and Y axis. The samples were warmed and mixed for 100 seconds at an intensity of 1, 10% duty cycle, and 1000 cycles per burst. Then the intensity was increased to 2 for 60 seconds. Finally, the cycles per burst were decreased to 200 for 60 seconds.

The processed BAL was filter-concentrated, hybridized, washed, and mounted as described in the Preferred Embodiments section. It was probed with species specific *S. aureus* TAMRA-labeled or universal bacteria fluorescein-labeled PNA probe.

Figure 5:
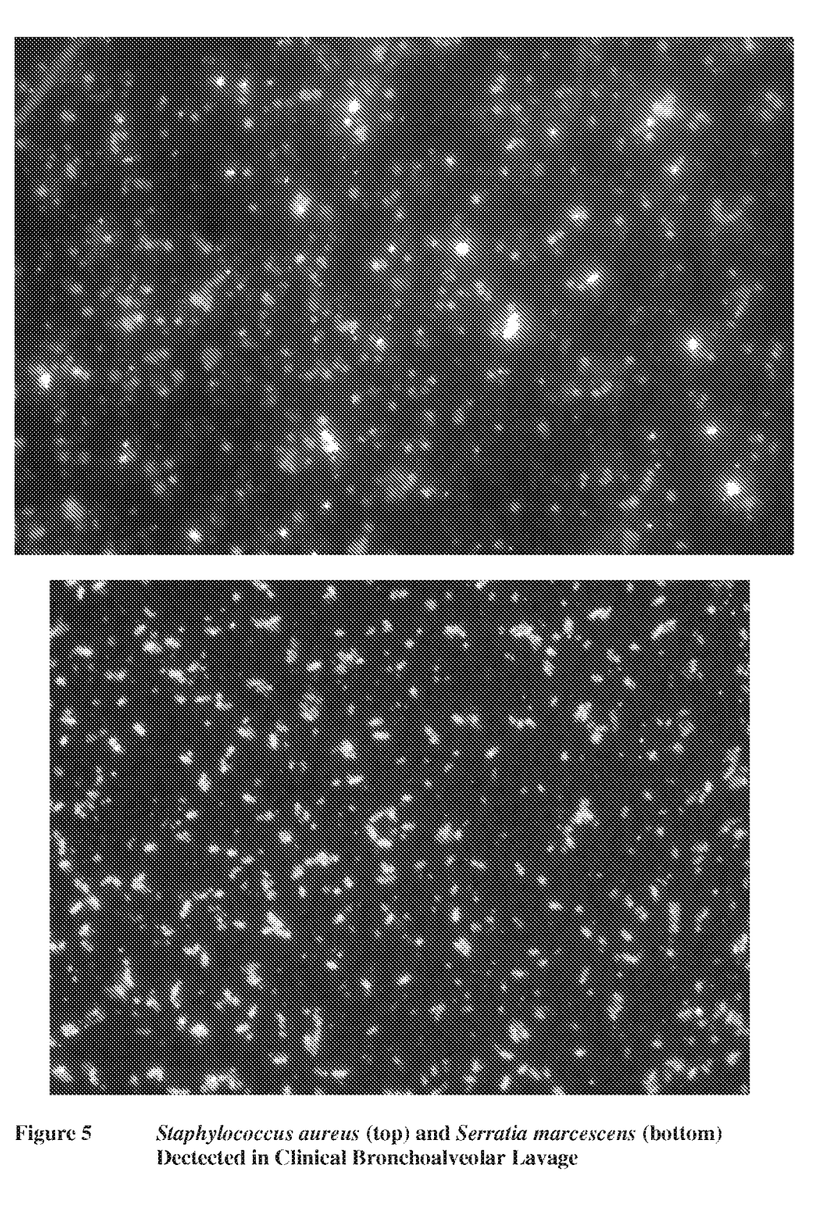
FIG. 5 are two panels that show the results of FISH experiments for the detection of *Staphylococcus aureus* (top) and *Serratia marcescens* (bottom) in clinical bronchoalveolar lavage.

The slide-bound membranes were examined using a fluorescent microscope, a 60× oil objective, and the AdvanDx PNA FISH filter cube (XF 53) for fluorescent organisms. *S. aureus* was detected in the BAL with reported *S. aureus*, and bacilli were detected in the BAL with reported *S. marcescens* (FIG. 5).

INCORPORATION BY REFERENCE

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

REFERENCES

1. Zierdt, C. H., Kagan, R. L. and J. D. MacLowry. 1977. Development of a Lysis-Filtration Blood Culture Technique. J. Clin. Microbiol. 5:46-50.
2. Zierdt, C. H. 1982. Blood-Lysing Solution Nontoxic to Pathogenic Bacteria. J. Clin. Microbiol. 15:172-174.
3. Oren, Z. and Shai, Y. 1997. Selective Lysis of Bacteria but Not Mammalian Cells by Diastereomers of Melittin: Structure-Function Study. Biochemistry. 36(7):1826-1835
4. Grifantini R, Bartolini E, Muzzi A, Draghi M, Frigimelica E, Berger J, Ratti G, Petracca R, Galli G, Agnusdei M, Giuliani M M, Santini L, Brunelli B, Tettelin H, Rappuoli R, Randazzo F, Grandi G. 2002. Previously unrecognized vaccine candidates against group B meningococcus identified by DNA microarrays. Nature Biotechnol 20: 914-21.
5. Seiter, J. A. and Jay, J. M. 1980. Application of Polyacrylamide Gel Electrophoresis to the Characterization and Identification of *Arthrobacter Species*. *Int. J. Syst. Bacteriol.*, 30:460-465
6. Zierdt, C. H. 1986. Simplified Lysed-Blood Culture Technique. J. Clin. Microbiol. 23:452-455.

We claim:

1. A method for selective lysis of endogenous cells in a biological sample comprising:
    contacting the biological sample with lysis solution comprising a detergent and a proteinase; and
    subjecting the mixture of the biological sample and lysis solution in a container immersed in a liquid bath to high-frequency ultrasound at a controlled temperature of between 20 and 40 degrees Celsius, wherein the high-frequency ultrasound selectively lyses endogenous cells in the biological sample;
    thereby selectively lysing the endogenous cells in the biological sample.

2. The method of claim 1, wherein the biological sample comprises endogenous cells and microorganisms.

3. The method of claim 1, wherein the endogenous cells are mammalian cells.

4. The method of claim 2, wherein the microorganisms are left substantially intact.

5. The method of claim 2, wherein the microorganisms are selected from the group consisting of: bacteria, yeast and fungi.

6. The method of claim 5, wherein the microorganisms are selected from the group consisting of: *Candida albicans, Candida krusei, Enterococcus faecium, Enterococcus faecalis, Escherichia coli, Klebsiella pneumoniae, Pseudomonas aeruginosa, Staphylococcus aureus, Staphylococcus epidermidis, Serratia marcescens, Enterobacter cloacae, Salmonella choleraesuis, Salmonella enteriditis, Streptococcus agalactiae, Propionibacterium acnes, Bacillus cereus, Staphylococcus lugdunensis*, Coagulase-negative staphylococci, *Streptococcus pneumoniae, Acinetobacter* (genus), *Enterobacter* (genus), *Proteus mirabilis, Proteus vulgaris, Stenotrophomonas maltophilia, Haemophilus influenzae, Candida parapsilosis, Candida tropicalis, Candida dubliniensis, Candida glabrata, Aspergillus fumigates, Aspergillus* (genus), *Mycobacterium tuberculosis, Clostridium difficile*.

7. The method of claim 1, further comprising isolating the biological sample from the subject.

8. The method of claim 1, wherein the temperature of the sample and lysis solution mixture is between 25 and 40 degrees Celsius.

9. The method of claim 1, further comprising the step of filtering the lysed sample.

10. The method of claim 1, further comprising the step of centrifuging the lysed sample.

11. The method of claim 9, wherein the filters have a pore size between 0.2 micron to 1 micron.

12. The method of claim 1, wherein the volume of lysis solution is less than 2× the sample volume.

13. The method of claim 1, wherein the detergent comprises: Saponin.

14. The method of claim 13, wherein the lysis solution further comprises Sodium Phosphate Buffer, pH 8.

15. The method of claim 13, wherein the Saponin is from *Quillaja* bark.

16. The method of claim 1, wherein the Proteinase is from *Aspergillus melleus*.

17. The method of claim 1, where the biological sample is a body fluid.

18. The method of claim 17, wherein the body fluid is selected from the group consisting of: blood or blood fractions, respiratory secretions, cerebrospinal fluid, urine, stool, wound exudates (pus), and naso-pharyngeal fluid/mucus.

19. The method of claim 1, where the biological sample selected from the group consisting of: platelets, platelet concentrate and a mammalian cell culture.

20. The method of claim 1, further comprising filtering or centrifuging the lysed sample; and
    detecting, identifying, characterizing or quantifying microorganisms in the biological sample;
    thereby detecting, identifying, characterizing or quantifying microorganisms in the biological sample.

21. The method of claim 20, wherein the detecting, identifying, characterizing or quantifying is carried out using peptide nucleic acid (PNA) fluorescent in suit hybridization (FISH).

22. The method of claim 17, wherein the biological sample is mucoid.

23. The method of claim 22, wherein the biological sample is selected from the group consisting of: sputum, endotracheal aspirate and bronchoalveolar lavage.

24. The method of claim 23, wherein the detergent comprises Tween 20.

25. A method for selective lysis of endogenous cells in a biological sample comprising:
    contacting the biological sample with lysis solution comprising saponin and a proteinase; and
    subjecting the mixture of the biological sample and lysis solution in a container immersed in a liquid bath to high-frequency ultrasound at a controlled temperature of between 20 and 40 degrees Celsius, wherein the high-frequency ultrasound selectively lyses endogenous cells in the biological sample;
    thereby selectively lysing the endogenous cells in the biological sample.

26. The method of claim 25, wherein the temperature of the sample and lysis solution mixture is between 25 and 40 degrees Celsius.

27. The method of claim 25, wherein the Saponin is from *Quillaja* bark.

28. The method of claim 25, wherein the Proteinase is from *Aspergillus melleus*.

29. The method of claim 25, wherein the lysis solution comprises 1.15% Saponin.

30. The method of claim 25, wherein the lysis solution comprises 11.25 Units Proteinase.

* * * * *

UNITED STATES PATENT AND TRADEMARK OFFICE
CERTIFICATE OF CORRECTION

PATENT NO. : 9,719,128 B2
APPLICATION NO. : 14/084026
DATED : August 1, 2017
INVENTOR(S) : Martin Fuchs et al.

It is certified that error appears in the above-identified patent and that said Letters Patent is hereby corrected as shown below:

In the Claims

In Claim 6 (Column 25, Line 46), replace "*Aspergillus fumigates*" with -- *Aspergillus fumigatus* --

In Claim 21 (Column 26, Line 27), replace "in suit" with -- *in situ* --

Signed and Sealed this
Fifth Day of December, 2017

Joseph Matal
*Performing the Functions and Duties of the*
*Under Secretary of Commerce for Intellectual Property and*
*Director of the United States Patent and Trademark Office*